(12) United States Patent
Polvino

(10) Patent No.: US 8,486,976 B2
(45) Date of Patent: Jul. 16, 2013

(54) ENHANCED MIGRAINE TREATMENTS BASED ON GHRELIN MIMETICS

(75) Inventor: William J. Polvino, Tinton Falls, NJ (US)

(73) Assignee: Helsinn Therapeutics (U.S.), Inc., Bridgewater, NJ (US)

( * ) Notice: Subject to any disclaimer, the term of this patent is extended or adjusted under 35 U.S.C. 154(b) by 302 days.

(21) Appl. No.: 12/713,531

(22) Filed: Feb. 26, 2010

(65) Prior Publication Data

US 2010/0222388 A1 Sep. 2, 2010

Related U.S. Application Data

(60) Provisional application No. 61/156,129, filed on Feb. 27, 2009.

(51) Int. Cl.
*A61K 31/40* (2006.01)
*A61K 31/405* (2006.01)

(52) U.S. Cl.
USPC ............ 514/359; 514/410; 514/412; 514/415

(58) Field of Classification Search
USPC .................. 514/359, 410, 412, 415
See application file for complete search history.

(56) References Cited

U.S. PATENT DOCUMENTS

| | | | |
|---|---|---|---|
| 5,767,085 A | 6/1998 | Johansen et al. | |
| 5,977,178 A | 11/1999 | Hansen et al. | |
| 6,060,499 A | 5/2000 | Plachetka | |
| 6,083,908 A | 7/2000 | Ankersen | |
| 6,274,584 B1 | 8/2001 | Peschke et al. | |
| 6,303,620 B1 | 10/2001 | Hansen et al. | |
| 6,384,034 B2 | 5/2002 | Simitchieva et al. | |
| 6,566,337 B1 | 5/2003 | Ankersen et al. | |
| 6,576,648 B2 | 6/2003 | Ankersen | |
| 6,849,597 B2 * | 2/2005 | Murata et al. | 514/8.3 |
| 6,919,315 B1 | 7/2005 | Peschke et al. | |

FOREIGN PATENT DOCUMENTS

WO  WO 2007/127207  11/2007

OTHER PUBLICATIONS

Gilmore et al. "Treatment of Acute Migraine Headache". Am Fam Physician. 2011,83(3):271-80.*
Doenicke et al. "Possible benefit of GR43175, a novel 5-HT1-like receptor agonist, for the acute treatment of severe migraine." *Lancet*, vol. 1, pp. 1309-1311, 1988.
Feniuk & Humphrey. "The Development of a Highly Selective 5-HT1 Receptor Agonist, Sumatriptan, for The Treatment of Migraine." Drug Development Research, vol. 26, pp. 235-240, 1992.
Smith et al. "Sumatriptan and naproxen sodium for the acute treatment of migraine." *Headache*, vol. 45, pp. 983-991, 2005.
De Ponti. "Pharmacology of emesis and gastrointestinal motility: implications for migraine." *Funct Neurol*, vol. 15(3), pp. 43-49, 2000.

* cited by examiner

*Primary Examiner* — Renee Claytor
(74) *Attorney, Agent, or Firm* — Arnall Golden Gregory LLP; Clark G. Sullivan

(57) ABSTRACT

The present invention relates to method of enhancing the absorption of migraine medications and thereby treating migraines by co-administering to a subject in need thereof an effective amount of a ghrelin mimetic or pharmaceutically acceptable salt, hydrate or solvate thereof and at least one migraine medication selected from a serotonin 5-HT$_{1B/1D}$ receptor agonist, a tryptamine derivative, an ergoline derivative, a non-steroidal anti-inflammatory drug, or an analgesic, or any combination thereof.

5 Claims, No Drawings

ENHANCED MIGRAINE TREATMENTS BASED ON GHRELIN MIMETICS

RELATED APPLICATIONS

The present application claims priority under 35 U.S.C. §119 to U.S. Ser. No. 61/156,129, filed Feb. 27, 2009.

BACKGROUND OF THE INVENTION

Migraines are widespread in the population and can have a significant impact on an individual's health and quality of life. In the U.S. alone, 18% of women and 6% of men report having had at least one migraine episode in the previous year (Silberstein, "Migraine". Lancet 2004; 363:381-391). Migraines can also have an economic impact due to medical expenses and reduced or lost work productivity. Migraines generally afflict young adults, the main population of the workforce. The unpredictable or periodic nature of migraines can result in temporary lost work productivity or extended work disability, let alone interfere with an individual's normal activities.

A migraine generally results in a specific type of vascular headache characterized by moderate to intense head pain, often described by sufferers as pulsing or throbbing, lasting up to 4-72 hours when untreated. The pain of a migraine is often localized to one side of the head (i.e., unilateral), although the pain may be present on both sides of the head (i.e., bilateral). Migraine headaches are also accompanied by at least one or more symptoms including extreme sensitivity to stimuli (e.g., light and sound), gastrointestinal upset and visual disturbances or aura.

Because the events that contribute to migraine are still not well understood, prevention and trigger avoidance are typically not effective in controlling migraines. More typically migraine sufferers rely on symptomatic control or abortive treatments for relieving individual headaches. Despite continuing advances in migraine treatment, most existing treatments work slowly, have limited efficacy, or have undesirable side effects.

Sumatriptan and other triptan molecules represent the dominant standard of care against migraine attacks. Sumatriptan is a serotonin ($5-HT_{1B/1D}$) receptor agonist that causes constriction of cranial blood vessels. Sumatriptan is widely prescribed in the United States and around the world as a treatment for acute migraine headaches with or without aura in adults. Sumatriptan succinate is marketed commercially as Imitrex® in tablet, nasal spray and injectable dosage forms. Doenicke et al., Lancet, 1988, Vol. 1, 1309-11; and Feniuk & Humphrey, Drug Development Research, 1992, 26, 235-40. Other marketed triptans that act as $5-HT_{1B/1D}$ receptor agonists include rizatriptan, eletriptan, zolmitriptan, naratriptan, almotriptan, and frovatriptan.

The triptans are reported to suffer from several disadvantages, including migraine reoccurrence. In particular, it has been observed that the migraine in patients who are treated with sumatriptan often reoccurs within 8 or 24 hours of an initial treatment. To overcome this problem, Plachetka et al., in U.S. Pat. No. 6,060,499, have proposed combining the sumatriptan with a long acting NSAID such as naproxen sodium. According to Plachetka, "the addition of a long-acting NSAID to a 5-HT agonist extends the period of effective anti-migraine action and prevents the relapse headache from occurring (or "rebound migraines"), whatever is its cause." See also Smith et al., HEADACHE 2005; 45:983-91; and U.S. Pat. No. 6,384,034 to Simitchieva et al. (proposing a combination of sumatriptan or rizatriptan and a selective COX-2 inhibitor such as rofecoxib or celecoxib.))

The triptans can also suffer from a slow pharmacokinetic profile and, consequently, a delayed therapeutic effect. In healthy adults, it requires on average 2.0 hours after administration for the sumatriptan to reach its maximum concentration in the plasma. During a migraine attack, the absorption slows even further, and maximum blood concentrations are not reached until 2.5 hours after administration. See prescribing information for Imitrex® tablets. Investigators have proposed that this increased absorption time is caused by a slowing of the gastrointestinal tract, but therapeutic interventions based on such delayed gastrointestinal motility remain evasive. See De Ponti et al., FUNCT NEUROL. 2000; 15 Suppl 3:43-9.

To overcome this delayed action, Maichle et al. (WO 2007/127207) have proposed combining the triptan with diclofenac, in a specially formulated dosage form that hastens the absorption of diclofenac in the GI tract. The combination is said to provide quick relief through the diclofenac, in as little as 15 minutes, before the triptan can take effect. While the dosage form has some utility, it still fails to solve the problem of triptan absorption, and the delayed therapeutic effect attainable by the triptan.

Accordingly, it is an object of the present invention to improve the absorption rate of triptans and other migraine medications when orally administered. Another object is to improve the absorption rate of triptans and other migraine medications when orally administered during a migraine attack.

Yet another object is to treat the symptoms associated with migraine, using a combined drug regimen, to provide relief greater than that achieved using a triptan or other migraine medication alone.

Thus, another object is the provision of a combined drug regimen that treats one or more symptoms often associated with migraine faster than a triptan or other migraine medication alone, wherein said symptoms are selected from nausea, photophobia, phonophobia, pain, and rebound headache.

In another embodiment the combined drug regimen treats one or more symptoms often associated with migraine better than a triptan or other migraine medication alone, wherein said symptoms are selected from nausea, photophobia, phonophobia, pain, and rebound headache.

SUMMARY OF THE INVENTION

The present invention relates to a method of treating a subject having a migraine, or preventing a migraine in a subject having a history of migraines or at risk of developing a migraine, by co-administering a ghrelin mimetic of the present invention and a migraine drug, and thereby enhancing the speed of absorption and/or therapeutic effect of the migraine drug. Thus, in one embodiment, the invention provides a method of enhancing the speed of absorption (or speed of therapeutic effect) of a second molecule selected from serotonin $5-HT_{1B/1D}$ receptor agonists, tryptamine derivatives, ergoline derivatives, non-steroidal anti-inflammatory drugs, and analgesics comprising administering to a subject having a migraine an effective amount of a ghrelin mimetic and the second molecule.

In another embodiment, the invention provides a method of treating a subject having a migraine comprising administering to the subject an effective amount of a ghrelin mimetic and a second molecule selected from serotonin $5-HT_{1B/1D}$ receptor agonists, tryptamine derivatives, ergoline derivatives, non-steroidal anti-inflammatory drugs, and analgesics.

In still another embodiment, the invention relates to the treatment, and improved speed of absorption and/or effectiveness, in patients suffering from complications or symptoms of migraine. Therefore, in still another embodiment the invention provides a method of treating one or more complications or symptoms of migraine, and/or enhancing the speed of absorption or therapeutic effect in a patient suffering from such complications or symptoms, wherein said complications or symptoms are selected from gastric stasis, nausea, vomiting, photophobia and phonophobia, comprising administering to a subject suffering from one or more of said complications or symptoms an effective amount of a ghrelin mimetic of the present invention and a second molecule selected from serotonin 5-HT$_{1B/1D}$ receptor agonists, tryptamine derivatives, ergoline derivatives, non-steroidal anti-inflammatory drugs, and analgesics.

The present invention further relates to a method of treating gastrointestinal upset and other conditions caused by a migraine. Gastrointestinal upset includes one or more of the symptoms of gastric stasis, emesis, nausea, or vomiting. The method involves administering to a subject in need thereof a therapeutically effective amount of a ghrelin mimetic of the present invention and at least one additional therapeutic agent, e.g., a serotonin 5-HT$_{1B/1D}$ receptor agonist, a tryptamine derivative, an ergoline derivative, a non-steroidal anti-inflammatory drug, an analgesic, or any combination thereof.

The invention further provides pharmaceutical compositions for the treatment of migraines comprising the ghrelin mimetics of the invention and at least one of a serotonin 5-HT1B/1D receptor agonist, a tryptamine derivative, an ergoline derivative, a non-steroidal anti-inflammatory drug, an analgesic, or any combination thereof.

The foregoing and other objects, features and advantages of the invention will be apparent from the following more particular description of preferred embodiments of the invention.

DETAILED DESCRIPTION OF THE INVENTION

The present invention may be understood more readily by reference to the following detailed description of preferred embodiments of the invention and the Examples included therein.

Definitions

As used in the specification and claims, the singular forms a, an and the include plural references unless the context clearly dictates otherwise. For example, the term a pharmaceutical excipient may refer to one or more pharmaceutical excipients for use in the presently disclosed formulations and methods.

When doses are given for a drug and its salt, it will be understood that the calculated dose is based on the molecular weight of the base drug, without including the weight of the salt moiety, unless stated to the contrary herein. Thus, the weight of the hydrochloride moiety in anamorelin hydrochloride would be excluded from the calculation.

When ranges are given by specifying the lower end of a range separately from the upper end of the range, it will be understood that the range can be defined by selectively combining any one of the lower end variables with any one of the upper end variables that is mathematically possible.

When used herein the term "about" will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent to the recited strength.

"Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In a preferred embodiment, the mammal is a human.

As used herein, "treating" and "treatment" refer to decrease, reduce, suppress, attenuate, diminish, arrest, stabilize, or eliminate the development, progression, or state of a disease or disorder. In the context of the invention, the methods, pharmaceutical compositions, and kits of the invention may be used to reduce or eliminate a migraine or symptoms of a migraine, e.g., headache, gastrointestinal upset, sensitivity to stimuli, in a subject.

As used herein, "prevent" and "prevention" refer to a decrease in the occurrence of a disorder or decrease in the risk of acquiring a disorder or its associated symptoms in a subject. In the context of the invention, the methods and compositions of the invention may be used to prevent a migraine or symptoms associated with a migraine in a subject. The prevention may be complete, e.g., the total absence of a migraine and/or its symptoms. The prevention may also be partial, such that the likelihood of the occurrence of the migraine is less likely to occur than had the subject not received the present invention.

Discussion

The present invention relates to a method of treating a subject having a migraine (e.g., common migraines or classic migraines). The present invention also relates to a method of preventing a migraine in a subject having a history of migraines or at risk of developing a migraine. The methods involve co-administering to a subject in need thereof a therapeutically effective amount of a ghrelin mimetic of the present invention and therapeutically effective amount of at least one additional therapeutic agent, e.g., a serotonin 5-HT$_{1B/1D}$ receptor agonist, a tryptamine derivative, an ergoline derivative, a non-steroidal anti-inflammatory drug, an analgesic, or any combination thereof. The additional therapeutic agent, e.g., serotonin 5-HT$_{1B/1D}$ receptor agonist, tryptamine derivative, ergoline derivative, non-steroidal anti-inflammatory drug, or analgesic, may be administered as a pharmaceutically acceptable salt, hydrate or solvate thereof.

The present invention further relates to a method of treating gastrointestinal upset and other conditions caused by a migraine. Gastrointestinal upset includes one or more of the symptoms of gastric stasis, emesis, nausea, or vomiting. The method involves administering to a subject in need thereof a therapeutically effective amount of a ghrelin mimetic and at least one additional therapeutic agent, e.g., a serotonin 5-HT$_{1B/1D}$ receptor agonist, a tryptamine derivative, an ergoline derivative, a non-steroidal anti-inflammatory drug, an analgesic, or any combination thereof. The ghrelin mimetic and serotonin 5-HT$_{1B/1D}$ receptor agonist, tryptamine derivative, ergoline derivative, non-steroidal anti-inflammatory drug, or analgesic may be administered as a pharmaceutically acceptable salts, hydrates or solvates thereof.

The invention further provides pharmaceutical compositions for the treatment of migraines comprising the ghrelin mimetics of the invention and at least one of a serotonin 5-HT$_{1B/1D}$ receptor agonist, a tryptamine derivative, an ergoline derivative, a nonsteroidal anti-inflammatory drug, an analgesic, or any combination thereof. The pharmaceutical compositions may further comprise one or more of a sedative, vasoconstrictor, or caffeine. Although preferably co-administered as a single pharmaceutical composition, the ghrelin mimetics and at least one of a serotonin 5-HT$_{1B/1D}$ receptor agonist, a tryptamine derivative, an ergoline derivative, a non-steroidal anti-inflammatory drug, an analgesic, or any combination thereof, may be co-administered individually.

Migraine

As used herein, the term "migraine" refers to a neurological disorder characterized by a headache, or migraine headache, and accompanying symptoms. However, the term "migraine" may also describe a neurological disorder encompassing such symptoms without headache, e.g., head-ache-free migraine and abdominal migraine. Additional types of headaches intended to be included within the scope of the invention and referred to herein as migraines include spontaneous migraines, visually-induced migraines, interictal period migraines, childhood periodic syndromes, retinal migraine and probable migraines.

A migraine generally results in a specific type of vascular headache characterized by moderate to intense head pain, often described by sufferers as pulsing or throbbing, lasting up to 4-72 hours when untreated. The pain of a migraine is often localized to one side of the head (i.e., unilateral), although the pain may be present on both sides of the head (i.e., bilateral). Migraine headaches are also accompanied by at least one or more symptoms including extreme sensitivity to stimuli (e.g., light and sound), gastrointestinal upset (e.g., nausea and vomiting), and visual disturbances or aura.

The two most prevalent types of migraines are the "common migraine" and the "classic migraine." Common migraines are experienced in about two-thirds of migraine sufferers. Classic migraines are estimated to occur in about one-fifth to one-third of migraine sufferers. The main difference between the two migraine types is the appearance of neurological phenomena that precede or accompany a classic migraine or "aura". An aura may be visual, sensory, or motor in nature. Visual aura is the most common type experienced in which a person may see flashing lights or zigzag lines, or may temporarily lose vision. Symptoms of classic migraines may also include speech difficulty, weakness of an arm or leg, tingling of the face or hands, and confusion. The methods, pharmaceutical compositions, and kits of the invention may be used to treat or prevent the types of migraines or the symptoms of such migraines described herein. Some sufferers are able to predict the onset of a migraine episode because it is preceded by visual aura. Prevention of migraines preceded by visual aura is contemplated.

Nausea and/or vomiting are also common symptoms of migraine. Not only does gastrointestinal upset cause discomfort, but impaired gastrointestinal motility can also hinder oral administration because of nausea and/or vomiting. In addition, gastric stasis can decrease the effectiveness of orally administered drugs by slowing their transport to the gut where they are absorbed. The invention also relates to relieving symptoms or conditions of gastrointestinal upset including, but not limited to, gastric stasis, nausea, vomiting, or any combination thereof.

The improved treatment of other symptoms and complications of migraine, such as photophobia and phonophobia, are also contemplated by the methods of the present invention. Thus, the combination of drugs can be used to treat various symptoms and conditions associated with migraine to a greater extent than either drug alone. The methods of the present invention can thus be defined as: A method of treating one or more symptoms or complications of migraine selected from headache pain, gastric stasis, nausea, vomiting, photophobia or phonophobia, comprising administering the combination of the present invention to a patient in need thereof, individually or in combination.

Thus, in various embodiments, the invention is used to treat, on an individual basis, Migraine, Headache Pain, Gastric Stasis, Nausea, Vomiting, Photophobia, or Phonophobia, and any combination thereof, including:

Migraine+gastric stasis
Migraine+headache pain+nausea+photophobia+phonophobia
Headache pain+nausea+photophobia+phonophobia
Headache pain+nausea
Headache pain+photophobia
Headache pain+phonophobia Gastroparesis Associated Disorders Gastroparesis, or gastric stasis, is a disorder of delayed gastric emptying in the absence of mechanical obstruction. It manifests clinically through a set of largely nonspecific symptoms such as early satiety, bloating, nausea, anorexia, vomiting, abdominal pain, and weight loss.

Gastroparesis becomes increasing problematic when it complicates the treatment of another disease, disorder or condition. One example of the complications caused by gastroparesis is the decreased efficacy of orally administered drugs. When the gastric motility is slowed, the rate of absorption of orally administered drugs in the gut also decreases creating complications for the treatment of these diseases, disorders and conditions.

Subjects with a number of diseases, disorders and conditions have been characterized as having gastroparesis. For example, subjects having diabetes, scleroderma, e.g., scleroderma of the stomach; psychiatric diseases, e.g., depression, and eating disorders (anorexia, bulimia); gastroesophageal reflux disease; atrophic gastritis; malignancy; endocrine and metabolic disorders, e.g., hypothyroidism, hypoparathyroidism and hyperparathyroidism; gallbladder disorders; post-cholecystectomy; cirrhosis and portal hypertension. Gastroparesis has also been associated with alcohol, smoking, and marijuana use.

Accordingly, the instant invention provides methods and compositions for treating subjects having diseases, conditions and disorders that result in gastroparesis. As described herein, the invention provides ghrelin mimetics and methods for co-administering these ghrelin mimetics in order to increase the gastric motility thereby allowing for an increased rate of absorption of the co-administered drug.

Growth Hormone Secretagogues/Ghrelin Mimetics

As used herein, "ghrelin mimetic" of the present invention refers to a substance (e.g., a molecule, a compound) which promotes (induces or enhances) at least one function characteristic of a ghrelin receptor (GRLN receptor, aka growth hormone secretagogue receptor (GHS-R$_{1a}$ receptor). Exemplary ghrelin mimetics are ghrelin agonists such as growth hormone secretagogues. In one embodiment, the ghrelin mimetic compound or ghrelin agonist binds to the GHS-R$_{1a}$ receptor or ghrelin receptor (i.e., is a ghrelin or GHS receptor agonist) and induces the secretion of growth hormone. A compound having GHS receptor agonist activity (e.g., a GHS receptor or ghrelin receptor agonist) can be identified and activity assessed by any suitable method. For example, the binding affinity of a GHS receptor agonist to the GHS receptor can be determined employing receptor binding assays and growth hormone stimulation can be assessed as described in U.S. Pat. No. 6,919,315, incorporated herein by reference.

Ghrelin receptors and GHS receptors are expressed in the hypothalamus, pituitary and pancreas, among other tissues. Activation of these receptors in the pituitary induces the secretion of growth hormone. In addition to inducing the secretion of growth hormone, recent studies have shown the growth hormone secretagogues and ghrelin mimetics can increase appetite and body weight. At typical doses, ghrelin mimetics are also known to induce the secretion of IGF-1. Exemplary ghrelin mimetic compounds are those described in U.S. Pat. Nos. 6,303,620, 6,576,648, 5,977,178, 6,566,337, 6,083,908, 6,274,584, and 6,919,315, and 5,767,085, the entire content of all of which are incorporated herein by reference.

Exemplary ghrelin mimetics are selected from anamorelin, ipamorelin, or compound 1141 as defined herein, or a pharmaceutically acceptable salt, hydrate, or solvate thereof. Anamorelin is chemically described as 3-Piperidinecarboxylic acid, 1-(2-methylalanyl-D-tryptophyl)-3-(phenylmethyl)-, trimethylhydrazide, (3R)-, or (3R)-1-{(2R)-2-[(2-amino-2-methylpropanoyl)amino]-3-(indol-3-yl)propanoyl}-3-benzyl-N,N',N'-trimethylpiperidine-3-carbohydrazide, and is represented by the following chemical structure:

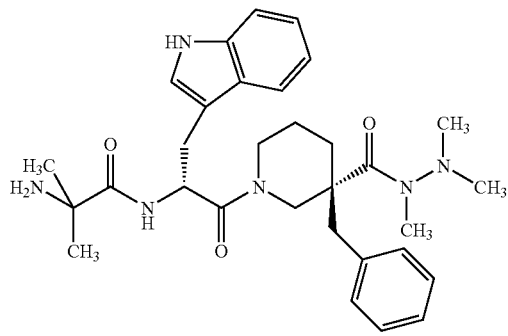

III

Compound 1141 is chemically described as (2E)-4-(1-Aminocyclobutyl)but-2-enoic acid N-((1R)-1-{N-[(1R)-1-benzyl-2-(4-hydroxypiperidin-1-yl)-2-oxoethyl]-N-methyl-carbamoyl}-2-(biphenyl-4-yl)ethyl)-N-methylamide, and is represented by the following chemical structure:

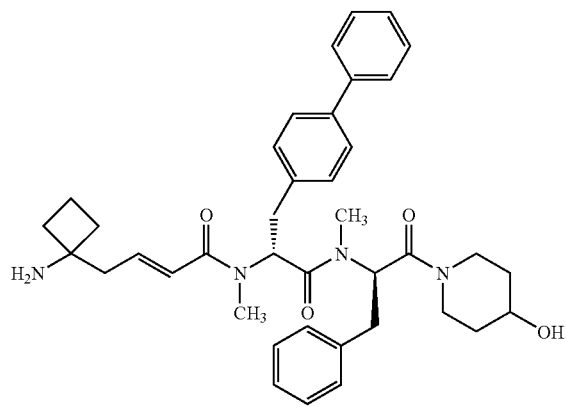

VI

Ipamorelin is chemically described as is chemically defined as α-Methylalanine-L-histidine-D-β-(2-naphthyl)-alanine-D-phenylalanine-L-lysinamide or H-Aib-His-β-(2-naphthyl)-D-Ala-D-Phe-Lys-NH$_2$, and has the following chemical structure:

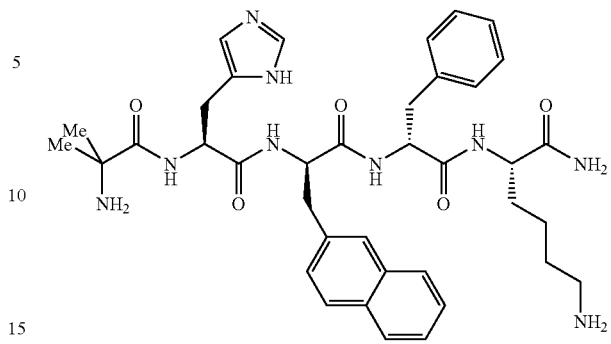

XIV

Serotonin 5-HT$_{1b/1d}$ Receptor Agonists

As used herein, "serotonin 5-HT$_{1B/1D}$ receptor agonist" refers to a drug that activates serotonin 5-HT$_{1B}$ and 5-HT$_{1D}$ receptors. Such compounds mimic the effect of the neurotransmitter serotonin and have been shown to be effective in treating migraines and symptoms of migraine. Without being bound to any particular theory, such agonists act to relieve migraines by activating serotonin 5-HT$_{1B}$ and 5-HT$_{1D}$ receptors in cranial blood vessels (causing their constriction) and subsequently inhibiting pro-inflammatory neuropeptide release. These drugs may also be effective because they act on serotonin receptors in nerve endings as well as the blood vessels. Exemplary serotonin 5-HT$_{1B/1D}$ receptor agonists for use with the invention include, but are not limited to triptans and some ergoline derivatives, e.g., ergotamine.

Tryptamine Derivatives

As used herein or "tryptamine derivative" or "triptan" refers to a drug derived from a monoamine alkaloid (i.e., tryptamine) which contains an indole ring structure, and is chemically related to the amino acid tryptophan. Tryptamine is found in trace amounts in the brains of mammals and is believed to play a role as a neuromodulator or neurotransmitter. Tryptamine derivatives include biologically active compounds, such as neurotransmitters and hallucinogens.

Triptans include, but are not limited to, sumatriptan, or 1-[3-(2-dimethylaminoethyl)-1H-indol-5-yl]-N-methyl-methanesulfonamide; rizatriptan, or N,Ndimethyl-2-[5-(1,2,4-triazol-1-ylmethyl)-1H-indol-3-yl]ethanamine; naratriptan, or Nmethyl-2-[3-(1-methyl-4-piperidyl)-1H-indol-5-yl]-ethanesulfonamide; zolmitriptan, or (4S)-4-{[3-(2-dimethylaminoethyl)-1H-indol-5-yl]methyl}-1,3-oxazolidin-2-one; eletriptan, or 3-[((2R)-1-methylpyrrolidin-2-yl)methyl]-5-(2-phenylsulfonylethyl)-1H-indole; almotriptan, or N,N-dimethyl-2-[5-(pyrrolidin-1-ylsulfonyl-methyl)-1H-indol-3-yl]-ethanamine; and frovatriptan, or 6-methylamino-6,7,8,9-tetrahydro-5H-carbazole-3-carboxamide. Without being bound to any particular theory, the action of triptans is attributed to their binding to serotonin 5-HT$_{1B}$ and 5-HT$_{1D}$ receptors in cranial blood vessels (causing their constriction) and subsequent inhibition of pro-inflammatory neuropeptide release. There is evidence to suggest that these drugs are effective because they act on serotonin receptors in nerve endings as well as the blood vessels. Exemplary triptans for use with the invention include, but are not limited to sumatriptan, rizatriptan, naratriptan, zolmitriptan, eletriptan, almotriptan, and frovatriptan.

A preferred dose of sumatriptan, when administered orally, ranges from about 25 to about 200 mg, from about 2 to about 8 mg or 4 mg when administered parenterally (particularly subcutaneous) and from 5 to 20 mg when administered intranasally. Additional dose ranges are, for eletriptan, 10-60 or 20-40; for rizatriptan, 2.5 to 20 or 5 to 10; for zolmitriptan, 1.5 to 7.5 or 2.5 to 5.0 mg; for naratriptan, 0.5 to 5.0 or 1.0 to 2.5 mg; for almotriptan, 2.5 to 15.0, or 6.25 to 12.5 mg; and for frovatriptan, 1.0 to 5.0 mg.

Ergoline Derivatives

As used herein or "ergoline derivative" refers to a drug derived from an ergoline alkaloids, which are found in fungi and plants. Ergoline derivatives are used in the treatment of migraine (sometimes in combination with caffeine) and clinically as a 5-$HT_1$ agonist for the purpose of vasoconstriction. Ergoline derivatives are toxic at high dose and some have psychedelic or hallucinogenic effects, but at low dose and/or with regulated use can ergoline derivatives can be used to treat migraines.

Ergoline derivatives include, but are not limited to, lysergic acids (e.g., Ergine, ergometrine, methylergometrine, methysergide, and lysergide); ergopeptines (e.g., Ergotamine, Ergocristine, Ergocornine, Ergocryptine, Bromocriptine, and Ergovaline); clavines (e.g., agroclavine, elymoclavine, and lysergol); pergolide; and lisuride. Exemplary ergoline derivatives suitable for use with the invention include, but are not limited to, Ergotamine, Ergine, ergometrine, methylergometrine, methysergide, lysergide, Ergocristine, Ergocornine, Ergocryptine, Bromocriptine, Ergovaline, Ergocristine, Ergocornine, Ergocryptine, Bromocriptine, Ergovaline, agroclavine, elymoclavine, lysergol, Pergolide, and Lisuride.

Non-Steroidal Anti-Inflammatory Drugs and Analgesics

As used herein, an "analgesic" refers to any member of the diverse group of drugs used to relieve pain. Analgesic drugs act in various ways on the peripheral and central nervous systems. Analgesic drugs include acetaminophen, non-steroidal anti-inflammatory drugs (NSAIDs) such as the salicylates, 2-arylpropionic acids, and COX-2 selective inhibitors, narcotic drugs such as morphine, synthetic drugs with narcotic properties such as tramadol, and various others. Exemplary analgesics for use with the invention include, but are not limited to, acetaminophen, and non-steroidal anti-inflammatory drugs. Acetaminophen and certain NSAIDs are typically inexpensive and available without a prescription.

As used herein, a "non-steroidal anti-inflammatory drug", or "NSAID", refers to a drug with analgesic, antipyretic and anti-inflammatory effects, i.e., capable of reducing pain, fever and inflammation. The term "non-steroidal" is used to distinguish these drugs from steroids, which have a similar anti-inflammatory action, but also have a broad range of other effects. As analgesics, NSAIDs are unusual in that they are non-narcotic.

NSAIDs include, but are not limited to, Salicylates (e.g., Aspirin, Amoxiprin, Benorilate, Choline magnesium salicylate, Diflunisal, Faislamine, Methyl salicylate, Magnesium Salicylate, and Salicyl salicylate (salsalate)); Arylalkanoic acids (e.g., Diclofenac, Aceclofenac, Acemetacin, Bromfenac, Etodolac, Indometacin, Nabumetone, Sulindac, and Tolmetin); 2-Arylpropionic acids (profens) (e.g., Ibuprofen, Carprofen, Fenbufen, Fenoprofen, Flurbiprofen, Ketoprofen, Ketorolac, Loxoprofen, Naproxen, Oxaprozin, Tiaprofenic acid, and Suprofen); N-Arylanthranilic acids (fenamic acids) (e.g., Mefenamic acid and Meclofenamic acid); Pyrazolidine derivatives (e.g., Phenylbutazone, Azapropazone, Metamizole, Oxyphenbutazone, and Sulfinpyrazone); Oxicams (e.g., Piroxicam, Lornoxicam, Meloxicam, and Tenoxicam); COX-2 Selective Inhibitors (e.g., Celecoxib, Etoricoxib, Lumiracoxib, Parecoxib, Rofecoxib, and Valdecoxib); Sulphonanilides (e.g., Nimesulide); Licofelone; and Omega-3 Fatty Acids. Common members of this group of drugs are aspirin, ibuprofen, and naproxen because they are inexpensive and commonly available without prescription. Exemplary NSAIDs for use with the invention include, but are not limited to, aspirin, ibuprofen, and naproxen.

As used herein, "therapeutically effective amount" refers to an amount sufficient to elicit the desired biological response. In the present invention, the desired biological response is treating or preventing a migraine.

The therapeutically effective amount or dose will depend on the age, sex and weight of the patient, and the current medical condition of the patient. The skilled artisan will be able to determine appropriate dosages depending on these and other factors to achieve the desired biological response. The dose of the primary medication, such as the triptan, will typically be the same dose that is used when the drug is administered individually.

A suitable dose for the ghrelin mimetic, which will typically be given with the same frequency as the primary medication, can be in the range of from about 0.1 mg to about 2,000 mg, or from 1 mg to 1000 mg. For anamorelin hydrochloride, which typically would be administered orally, a preferred daily dose is in the range of 10 mg to 300 mg, 20 mg to 200 mg, or 25 mg to 100 mg. For ipamorelin diacetate, which typically would be administered parenterally, a preferred is in the range of 0.5 mg to 40 mg, 1.0 to 25 mg, or 2.0 to 15 mg.

Combination Administration

Administration of a ghrelin mimetic can take place prior to, after or at the same time as treatment with an additional therapeutic agent, such as, for example, one or more additional agents for treating migraine, including those disclosed herein. As used herein, "combination administration" or "co-administration" refers to the administration of at least two therapeutic agents within a given time frame. Co-administration does not imply any particular order that at least two therapeutic agents must be administered. The therapeutic agents may be administered individually at about the same time or may be administered simultaneously by virtue of being present in the same pharmaceutical composition.

Pharmaceutical Compositions and Modes of Administration

The ghrelin mimetic of the invention can be incorporated into pharmaceutical compositions. Such compositions typically include the ghrelin mimetic and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. Such supplementary active compounds include, but are not limited to sedatives, vasoconstrictors, and caffeine.

The pharmaceutical compositions can be included in a container, pack, or dispenser together with instructions for administration.

A pharmaceutical composition is formulated to be compatible with its intended route of administration. Examples of routes of administration include parenteral, oral, transmucosal, and rectal administration. The compounds for use in the method of the invention can be formulated for administration by any suitable route, such as for oral or parenteral, for example, transmucosal (e.g., sublingual, lingual, (trans)buccal), nasal, (trans)dermal, and (trans)rectal) administration.

Suitable compositions and dosage forms include tablets, capsules, caplets, pills, gel caps, troches, dispersions, suspensions, solutions, syrups, granules, beads, gels, powders, pellets, magmas, lozenges, discs, suppositories, liquid sprays, or dry powders.

It is preferred that the compounds are orally administered. Suitable oral dosage forms include, for example, tablets, capsules or caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycolate); or wetting agents (e.g., sodium lauryl sulphate). If desired, the tablets can be coated, e.g., to provide for ease of swallowing or to provide a delayed release of active, using suitable methods. Liquid preparation for oral administration can be in the form of solutions, syrups or suspensions. Liquid preparations (e.g., solutions, suspensions and syrups) are also suitable for oral administration and can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

As used herein, the term "pharmaceutically acceptable salt" refers to a salt of a compound to be administered prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The ghrelin mimetics disclosed can be present in the form of any pharmaceutically acceptable salt, although the hydrochloride salt is preferred for anamorelin, and the diacetate salt is preferred for ipamorelin. The primary active ingredient, such as the triptan, can also be present in the form of any pharmaceutically acceptable salt. In like manner, the active ingredients can be present as their hydrates, such as hemihydrate, monohydrate, dihydrate, trihydrate, tetrahydrate and the like and as solvates.

EXEMPLIFICATION

A pharmacokinetic study was performed with sumatriptan succinate (25 mg/dose), to evaluate the impact of an orally administered ghrelin mimetic of the present invention, anamorelin hydrochloride (100 mg/dose, based on weight of salt) on the bioavailability of the orally administered sumatriptan, when administered at the same time. The study was a two period crossover study in 22 healthy, normal men and women ages 18-45 years, conducted in open label format. Sumatriptan was administered as one oral tablet; anamorelin was administered as 4 25 mg oral capsules; and all medication was given with 200 mL of water. Subjects were fasted overnight with a seven day wash out period between periods. Plasma PK samples taken 10 minutes prior to dosing and at 15 min, 30 min, 45 min, 1 hour, 1.25 hours, 1.5 hours, 2 hours, 2.5 hours, 3 hours, 3.5 hours, and 4 hours postdose. All samples were analyzed using a validated bioanalytical method (LC-MS-MS). Results are reported in below in tables 1 and 2:

TABLE 1

| Parameter | Statistic | Anamorelin HCl + Sumatriptan (N = 22) | Sumatriptan (N = 22) | p-value | 90% CI for Trt Diff |
|---|---|---|---|---|---|
| Cmax (ng/mL) | N | 22 | 22 | 0.8021 | |
| | Mean | 20.25 | 20.26 | 0.2472 | |
| | Std Dev | 5.114 | 6.238 | 0.9039 | −2.11, 1.83 |
| | % CV | 25.3 | 30.8 | | |
| | Median | 21.25 | 20.45 | | |
| | Range | 9.84, 28.80 | 7.59, 31.70 | | |
| Tmax (minutes) [2] | N | 22 | 22 | | |
| | Mean | 49.82 | 67.09 | | |
| | Std Dev | 19.839 | 31.915 | 0.0213 | −20.00, 0.00 |
| | % CV | 39.8 | 47.6 | | |
| | Median | 45.00 | 53.00 | | |
| | Range | 30.00, 90.00 | 45.00, 180.00 | | |

TABLE 2

| Parameter | Statistic | Anamorelin HCl + Sumatriptan (N = 22) | Sumatriptan (N = 22) | p-value | 90% CI for Trt Diff |
|---|---|---|---|---|---|
| AUC 0-30 (ng * h/mL) | N | 22 | 22 | 0.1881 | |
| | Mean | 2.88 | 2.53 | 0.7432 | |
| | Std Dev | 1.178 | 1.295 | 0.0908 | 0.01, 0.68 |
| | % CV | 40.9 | 51.3 | | |
| | Median | 2.99 | 2.56 | | |
| | Range | 0.91, 5.78 | 0.53, 5.03 | | |
| AUC last (ng * h/mL) | N | 22 | 22 | 0.8421 | |
| | Mean | 42.27 | 45.56 | 0.0391 | |
| | Std Dev | 12.044 | 14.148 | 0.0666 | −5.63, −0.33 |
| | % CV | 28.5 | 31.1 | | |
| | Median | 45.39 | 45.44 | | |
| | Range | 20.02, 67.32 | 15.57, 68.07 | | |

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All references cited herein, including patents, patent applications, and published patent applications, are hereby incorporated by reference in their entireties, whether or not each is further individually incorporated by reference.

What is claimed is:

1. A method of enhancing the speed of absorption of sumatriptan or a pharmaceutically acceptable salt thereof comprising administering to a subject having a migraine an effective amount of a anamorelin or a pharmaceutically acceptable salt thereof and the sumatriptan or pharmaceutically acceptable salt thereof.

2. The method of claim 1, further comprising treating two or more complications or symptoms of migraine in said subject, wherein said complications or symptoms are selected from nausea, photophobia and phonophobia.

3. The method of claim 1, wherein said migraine is associated with gastrointestinal upset characterized by gastric stasis, nausea, or vomiting.

4. A method of treating the complications or symptoms of migraine, wherein said complications or symptoms are selected from gastric stasis, nausea, vomiting, photophobia and phonophobia, comprising administering to a subject suffering from one or more of said complications or symptoms an effective amount of anamorelin or a pharmaceutically acceptable salt thereof and a second molecule, wherein the second molecule is sumatriptan or a pharmaceutically acceptable salt thereof.

5. The method of claim 1 wherein said anamorelin or a pharmaceutically acceptable salt thereof is administered in a dose of from about 20 to about 200 mg, based on the weight of the free base.

* * * * *